United States Patent
Tanabe et al.

(10) Patent No.: US 12,274,502 B2
(45) Date of Patent: Apr. 15, 2025

(54) IMAGE PROCESSING METHOD, PROGRAM, IMAGE PROCESSING DEVICE, AND OPHTHALMIC SYSTEM

(71) Applicant: NIKON CORPORATION, Tokyo (JP)

(72) Inventors: Yasushi Tanabe, Fujisawa (JP); Mariko Hirokawa, Yokohama (JP)

(73) Assignee: NIKON CORPORATION, Tokyo (JP)

(*) Notice: Subject to any disclaimer, the term of this patent is extended or adjusted under 35 U.S.C. 154(b) by 1162 days.

(21) Appl. No.: 17/071,583

(22) Filed: Oct. 15, 2020

(65) Prior Publication Data
US 2021/0022606 A1 Jan. 28, 2021

Related U.S. Application Data

(63) Continuation of application No. PCT/JP2019/016652, filed on Apr. 18, 2019.

(30) Foreign Application Priority Data

Apr. 18, 2018 (JP) ................. 2018-080273

(51) Int. Cl.
*A61B 3/12* (2006.01)
*A61B 3/00* (2006.01)
*A61B 3/14* (2006.01)
*G06T 7/00* (2017.01)

(52) U.S. Cl.
CPC .......... *A61B 3/1241* (2013.01); *A61B 3/0025* (2013.01); *A61B 3/14* (2013.01); *G06T 7/0012* (2013.01); *G06T 2207/30041* (2013.01)

(58) Field of Classification Search
CPC .......... A61B 3/0025; A61B 3/12; A61B 3/14; A61B 3/1241; A61B 3/1225; A61B 3/102; A61B 3/1025; G06T 7/0012; G06T 7/73; G06T 2207/10024; G06T 2207/30041
See application file for complete search history.

(56) References Cited

FOREIGN PATENT DOCUMENTS

| CN | 104334173 A | 2/2015 |
| JP | H08-71045 A | 3/1996 |
| JP | 2008-284005 A | 11/2008 |
| WO | WO-2013/163758 A1 | 11/2013 |

OTHER PUBLICATIONS

Hirahara, et al., "Densitometry of Choroidal Vessels in Eyes With and Without Central Serous Chorioretinopathy by Wide-Field Indocyanine Green Angiography", American Journal of ophthalmology[online], 2006, vol. 166, 103-111.
Noda, "Funduscopic examination and photographing method, and future prospects, 2017 Ophthalmological Optics Tutorial Seminar—For ophthalmologist, orthoptist, optical engineers—", The Japanese Society of Ophthalmological Optics, Japan Optomechatronics Association, Aug. 19, 2017, p. 40.
CN Office Action issued in corresponding Chinese patent application dated Dec. 7, 2023 (13 pages).
Zhang, "Configuration and distributing of vortex vein by indocyanine green angiography," China Journal of Chinese Ophthalmology, Nov. 2003 (pp. 208-209).

*Primary Examiner* — Jack Dinh
(74) *Attorney, Agent, or Firm* — Foley & Lardner LLP

(57) ABSTRACT

In the present invention, vortex vein positions are detected from a fundus image. The image processing method comprising: a step in which a choroidal blood vessel structure is analyzed from a fundus image; and a step in which vortex vein positions are detected based on the choroidal blood vessel structure.

13 Claims, 16 Drawing Sheets

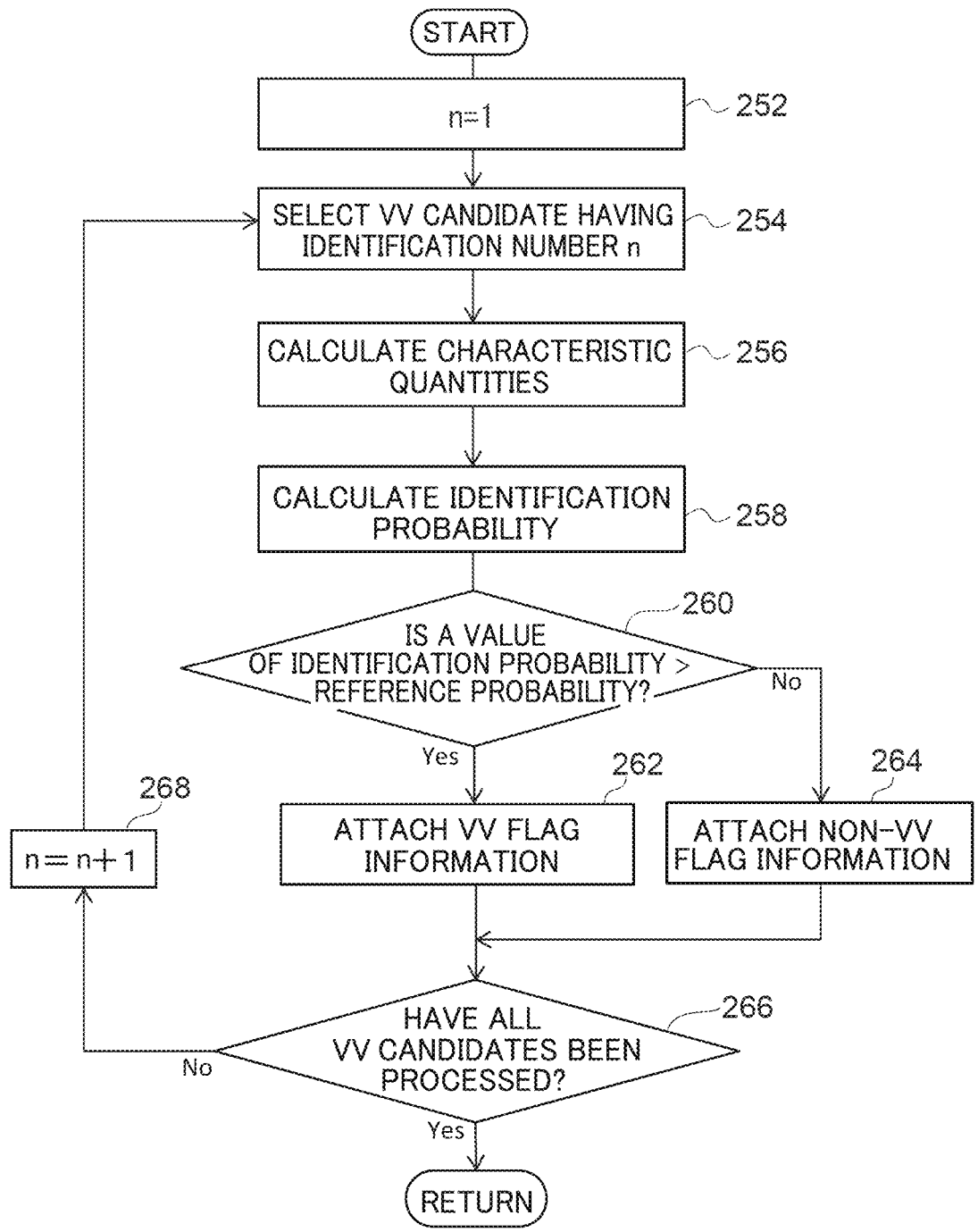

FOR A VV

NUMBER: 1

FOR A NON-VV

NUMBER: 2

IMAGE PROCESSING METHOD, PROGRAM, IMAGE PROCESSING DEVICE, AND OPHTHALMIC SYSTEM

CROSS-REFERENCE TO RELATED APPLICATIONS

This application is a continuation application of International Application No. PCT/JP2019/016652 filed Apr. 18, 2019, the disclosure of which is incorporated herein by reference in its entirety. Further, this application claims priority from Japanese Patent Application No. 2018-080273, filed Apr. 18, 2018, the disclosure of which is incorporated herein by reference in its entirety.

TECHNICAL FIELD

The technology of the present disclosure relates to an image processing method, a program, an image processing device, and an ophthalmic system.

RELATED ART

Technology is disclosed in Japanese Unexamined Patent Application Laid-Open (JP-A) No. H8-71045 that displays arteries and veins of a choroidal blood vessel in mutually different colors.

SUMMARY

An image processing method of a first aspect of the technology of the present disclosure includes step in which a choroidal blood vessel structure is analyzed from a fundus image, and a step in which vortex vein positions are detected based on this blood vessel structure.

An image processing device of a second aspect of the technology of the present disclosure has an image processing unit that analyzes a choroidal blood vessel structure from a fundus image, and detects vortex vein positions based on this blood vessel structure.

A program of a third aspect of the technology of the present disclosure causes a computer to execute the image processing method of the first aspect.

An ophthalmic system of a fourth aspect of the technology of the present disclosure is provided with a server that includes an image processing unit that analyzes a choroidal blood vessel structure from a fundus image, and detects vortex vein positions based on this blood vessel structure, and with a viewer that displays a vortex vein position-superimposed fundus image in which marks showing the vortex vein positions are displayed superimposed on the fundus image.

An image processing method of a fifth aspect of the technology of the present disclosure includes a step in which a choroidal blood vessel image is generated, and a step in which the choroidal blood vessel image is analyzed, and vortex vein positions are detected.

An image processing device of a sixth aspect of the technology of the present disclosure is provided with an image processing unit that generates a choroidal blood vessel image, analyzes the choroidal blood vessel image, and detects positions of vortex veins, a display control unit that generates a vortex vein position-superimposed fundus image in which marks showing the vortex vein positions are superimposed on the choroidal blood vessel image, and an output unit that outputs the vortex vein position-superimposed fundus image.

BRIEF DESCRIPTION OF THE DRAWINGS

FIG. 13 is a flowchart for a VV identification processing program.

DETAILED DESCRIPTION

Hereinafter, an exemplary embodiment of the present invention will be described in detail with reference to the drawings. Note that, in the following, in order to facilitate the description, a scanning laser ophthalmoscope is abbreviated to an 'SLO'.

Figure 1:
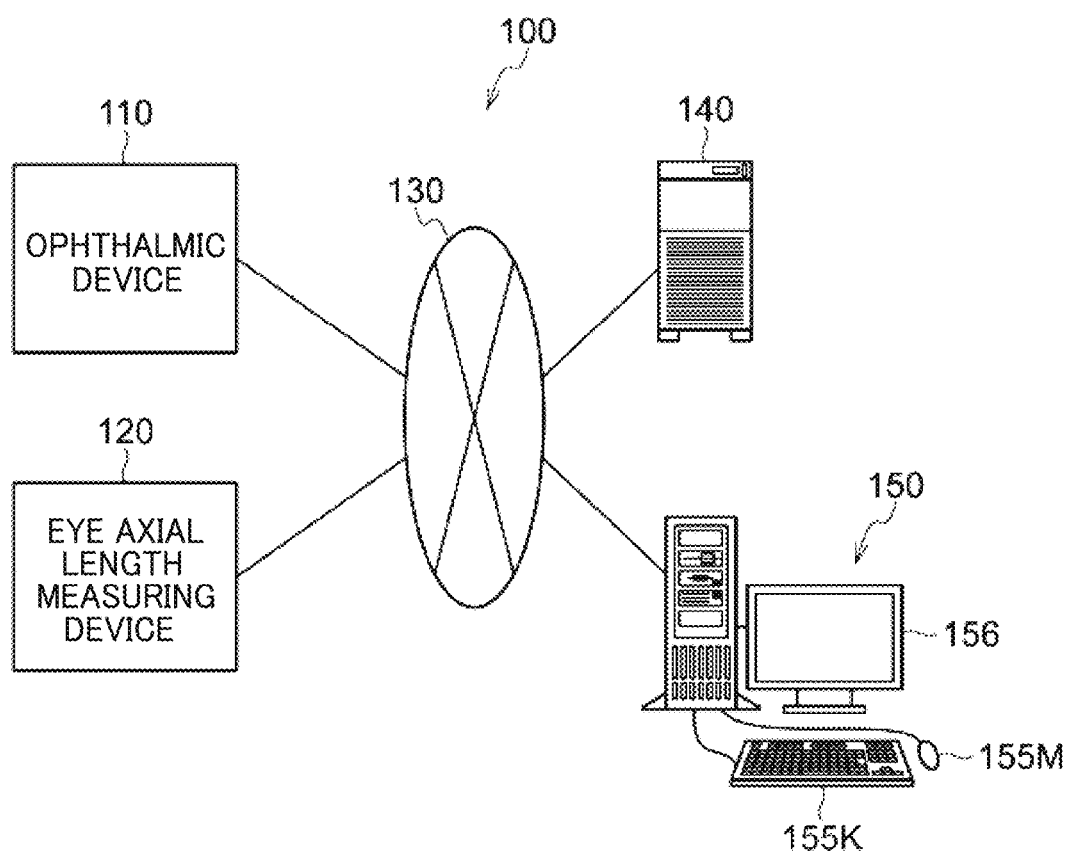
FIG. 1 is a block diagram of an ophthalmic system 100.

A structure of an ophthalmic system 100 will be described with reference to FIG. 1. As is shown in FIG. 1, the ophthalmic system 100 is provided with an ophthalmic device 110, an eye axial length measurement device 120, a management server device (hereinafter, referred to as a 'management server') 140, and an image display device (hereinafter, referred to as an 'image viewer') 150. The ophthalmic device 110 acquires fundus images. The eye axial length measurement device 120 measures an eye axial length of a patient. The management server 140 stores a plurality of fundus images and eye axial lengths that are obtained by photographing the fundus of a plurality of patients using the ophthalmic device 110. The stored fundus images and eye axial lengths are matched with an ID of the corresponding patient. The image viewer 150 displays fundus images acquired by the management server 140.

The management server 140 is an example of a 'server' of the technology of the present disclosure. The image viewer 150 is an example of a 'viewer' of the technology of the present disclosure.

The ophthalmic device 110, eye axial length measurement device 120, management server 140, and image viewer 150 are mutually connected to each other via a network 130.

Note that it is also possible for other ophthalmical instruments (i.e., examination instruments for OCT (Optical Coherence Tomography) measurement, field of vision measurement, and tonometric measurement ad the like) and diagnostic supporting devices that perform image analysis using artificial intelligence to also be connected via the network 130 to the ophthalmic device 110, the eye axial length measurement device 120, the management server 140, and the image viewer 150.

Figure 2:
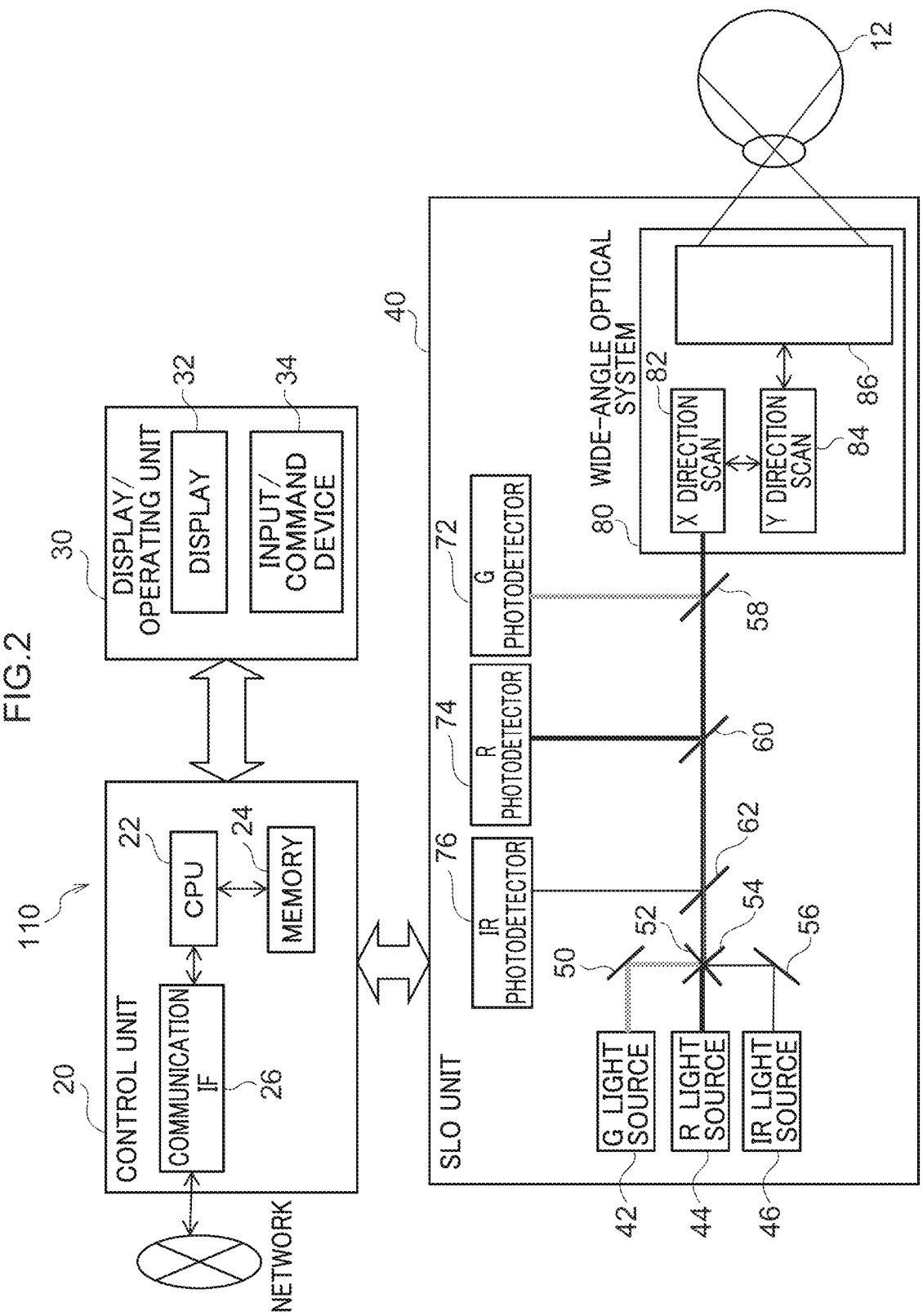
FIG. 2 is a schematic structural view showing an overall structure of an ophthalmic device 110.

Next, the structure of the ophthalmic device 110 will be described with reference to FIG. 2. As is shown in FIG. 2, the ophthalmic device 110 is provided with a control unit 20, a display/operating unit 30, and an SLO unit 40, and photographs a posterior segment (i.e., a fundus) of an eye 12 that is being examined. In addition, the ophthalmic device 110 may also be provided with an OCT unit (not shown in the drawings) that acquires OCT data about the fundus.

The control unit 20 is provided with a CPU 22, memory 24, and a communication interface (I/F) 26 and the like. The display/operating unit 30 is a graphic user interface that displays images obtained via photography, and receives various commands including a command to take a photograph, and is provided with a display 32 and an input/command device 34 such as a touch panel.

The SLO unit 40 is provided with a light source 42 for G light (i.e., green light: having a wavelength of 530 nm), a light source 44 for R light (i.e., red light: having a wavelength of 650 nm), and a light source 46 for IR light (i.e., infrared light (near infrared light): having a wavelength of 800 nm). The light sources 42, 44, and 46 emit their respective types of light upon receiving a command from the control unit 20.

The SLO unit 40 is provided with optical systems 50, 52, 54 and 56 that reflector transmit the light from the light sources 42, 44, and 46 so as to guide the light to a single optical path. The optical systems 50 and 56 are mirrors, while the optical systems 52 and 54 are beam splitters. The G light is reflected by the optical systems 50 and 54, the R light is transmitted through the optical systems 52 and 54, and the IR light is reflected by the optical systems 52 and 56, and each of these types of light is guided to the same optical path.

The SLO unit 40 is also provided with a wide-angle optical system 80 that scans the light from the light sources 42, 44, and 46 two-dimensionally across the posterior portion (i.e., the fundus) of the eye being examined 12. The SLO unit 40 is provided with a beam splitter 58 that reflects the G light out of the light from the posterior portion (i.e., the fundus) of the eye being examined 12, and transmits light other than the G light. The SLO unit 40 is also provided with a beam splitter 60 that reflects the R light out of the light transmitted through the beam splitter 58, and transmits light other than the R light. In addition, the SLO unit 40 is provided with a beam splitter 62 that reflects the IR light out of the light transmitted through the beam splitter 60. The SLO unit 40 is also provided with a G photodetector 72 that detects the G light reflected by the beam splitter 58, an R photodetector 74 that detects the R light reflected by the beam splitter 60, and an IR photodetector 76 that detects the IR light reflected by the beam splitter 62.

The wide-angle optical system 80 is provided with an X-direction scanning device 82 that is formed by a polygon mirror that scans the light from the light sources 42, 44, and 46 in an X direction, a Y-direction scanning device 84 that is formed by a galvanic mirror that scans this light in a Y direction, and an optical system 86 that includes a slit mirror and an elliptical mirror (not shown in the drawings) and widens the angle of the scanned light. The field of view (FOV) of the fundus is set to a wider angle by the optical system 86 than is achievable via the conventional technology, and it is possible to photograph a wider range of the fundus region than is achievable via the conventional technology. More specifically, as an external light irradiation angle from the outside of the eye being examined 12, it is possible to photograph a wide range of approximately 120 degrees of the fundus region (i.e., approximately 200 degrees as an internal light irradiation angle that is essentially capable of being photographed as a result of the fundus of the eye being examined 12 being irradiated with scanning light, when a center O of the eyeball of the eye being examined 12 is taken as a reference position). The optical system 86 may also be formed using a plurality of lens groups instead of using the slit mirror and elliptical mirror. In addition, two-dimensional scanners formed using MEMS mirrors may also be used for the respective scanning devices used for the X-direction scanning device 82 and the Y-direction scanning device 84.

When a system that includes a slit mirror and an elliptical mirror is used as the optical system 86, then it is possible to employ a structure in which a system that utilizes an elliptical mirror described in International Patent Application No. PCT/JP2014/084619 and in International Patent Application No. PCT/JP2014/084630 is used. The disclosures of International Patent Application No. PCT/JP2014/084619 (International Patent No. WO 2016/103484) filed internationally on Dec. 26, 2014, and of International Patent Application No. PCT/JP2014/084630 (International Patent No. WO 2016/103489) filed internationally on Dec. 26, 2014 are incorporated by reference in their entireties into the present application.

Note that the 'X direction' refers to a horizontal direction when the ophthalmic device 110 is placed on a horizontal surface, the 'Y direction' refers to a direction that is perpendicular to this horizontal surface, and a 'Z direction' refers to a direction that connects the center of the eyeball and the center of the pupil of an anterior segment of the eye being examined 12. Accordingly, the X direction, the Y direction, and the Z direction are mutually perpendicular to each other.

A color image of the fundus is obtained by photographing the fundus of the eyeball being examined 12 simultaneously using G light and R light. More specifically, the control unit 20 controls the light sources 42 and 44 such that they emit light simultaneously, and the G light and R light are scanned by the wide-angle optical system 80 across the fundus of the eye being examined 12. The G light reflected from the fundus of the eye being examined 12 is then detected by the G photodetector 72, and image data of a second fundus image (i.e., a G fundus image) is generated by the CPU 22 of the ophthalmic device 110. In the same way, the R light reflected from the fundus of the eye being examined 12 is detected by the R photodetector 74, and image data of a first fundus image (i.e., an R fundus image) is generated by the CPU 22 of the ophthalmic device 110. In addition, when IR light is reflected, the IR light reflected from the fundus of the eye being examined 12 is detected by the IR photodetector 76, and image data of an IR fundus image is generated by the CPU 22 of the ophthalmic device 110.

The CPU 22 of the ophthalmic device 110 mixes the first fundus image (i.e., the R fundus image) and the second fundus image (i.e., the G fundus image) together at a predetermined ratio, and displays the result as a color fundus image on the display 32. Note that instead of a color fundus image, it is also possible for the first fundus image (i.e., the R fundus image), the second fundus image (i.e., the G fundus image), or the IR fundus image to be displayed.

The image data for the first fundus image (i.e., the R fundus image), the image data for the second fundus image (i.e., the G fundus image), and the image data for the IR fundus image are sent from the ophthalmic device 110 to the management server 140 via a communication I/F 166. Each type of fundus image is used in the generation of a choroidal blood vessel image.

The eye axial length measurement device 120 shown in FIG. 1 has two modes, namely, a first mode and a second mode that are used to measure the eye axial length, which is the length in the eye axial direction (i.e., the Z direction) of the eye being examined 12. In the first mode, light from a light source (not shown in the drawings) is guided onto the eye being examined 12. Next, interference light generated by reflection light from the fundus and reflection light from the cornea is received, and the eye axial length is measured based on an interference signal showing the received interference light. In the second mode, the eye axial length is measured using ultrasonic waves (not shown in the drawings). The eye axial length measurement device 120 transmits the eye axial length measured using either the first mode or the second mode to the management server 140. It is also possible for the eye axial length to be measured using both the first mode and the second mode and, in this case, an average of the eye axial lengths measured using both modes is transmitted to the management server 140 as being the eye axial length. The eye axial length is saved as one item of patient data in the patient information held in the management server 140, and is also used for analyzing fundus images.

Figure 3:
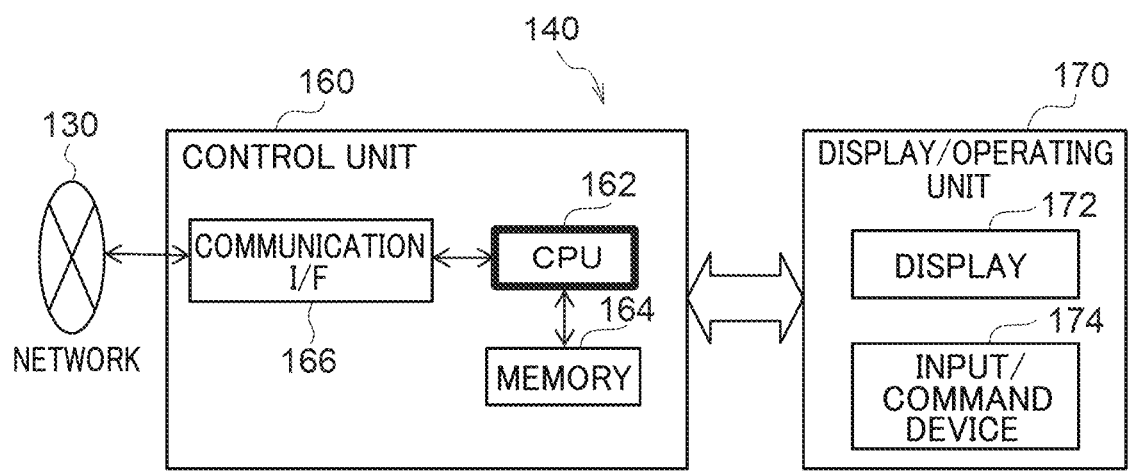
FIG. 3 is a block diagram showing a structure of an electrical system of a management server 140.

Next, a structure of the management server 140 will be described with reference to FIG. 3. As is shown in FIG. 3, the management server 140 is provided with a control unit 160 and a display/operating unit 170. The control unit 160 is provided with a computer which includes a CPU 162, memory 164 which serves as a storage device, and a communication interface (I/F) 166 and the like. An image processing program is stored in the memory 164. The display/operating unit 170 is a graphic user interface that displays images, and receives various commands, and is provided with a display 172 and an input/command device 174 such as a touch panel.

The structure of the image viewer 150 is the same as that of the management server 140 and, therefore, no description thereof will be given.

Figure 4:
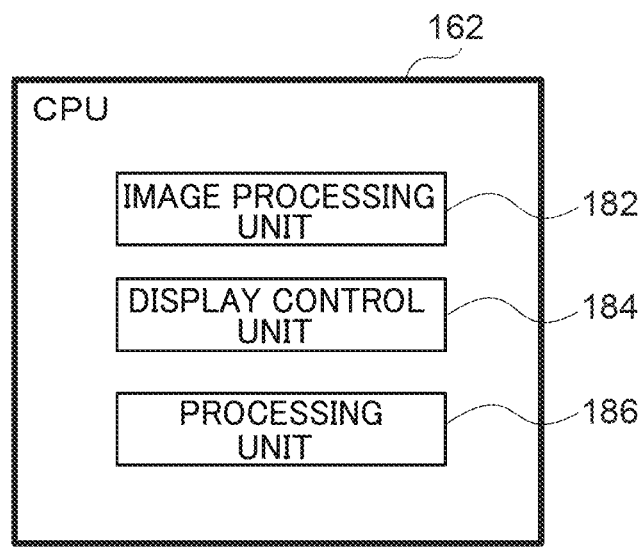
FIG. 4 is a block diagram showing functions of a CPU 162 of the management server 140.

Next, each of the various functions that are performed as a result of the CPU 162 of the management server 140 executing an image processing program will be described with reference to FIG. 4. The image processing program is provided with an image processing function, a display control function, and a processing function. As a result of the CPU 162 executing the image processing program having each of these functions, as is shown in FIG. 4, the CPU 162 is able to function as an image processing unit 182, a display control unit 184, and a processing unit 186.

Figure 5:
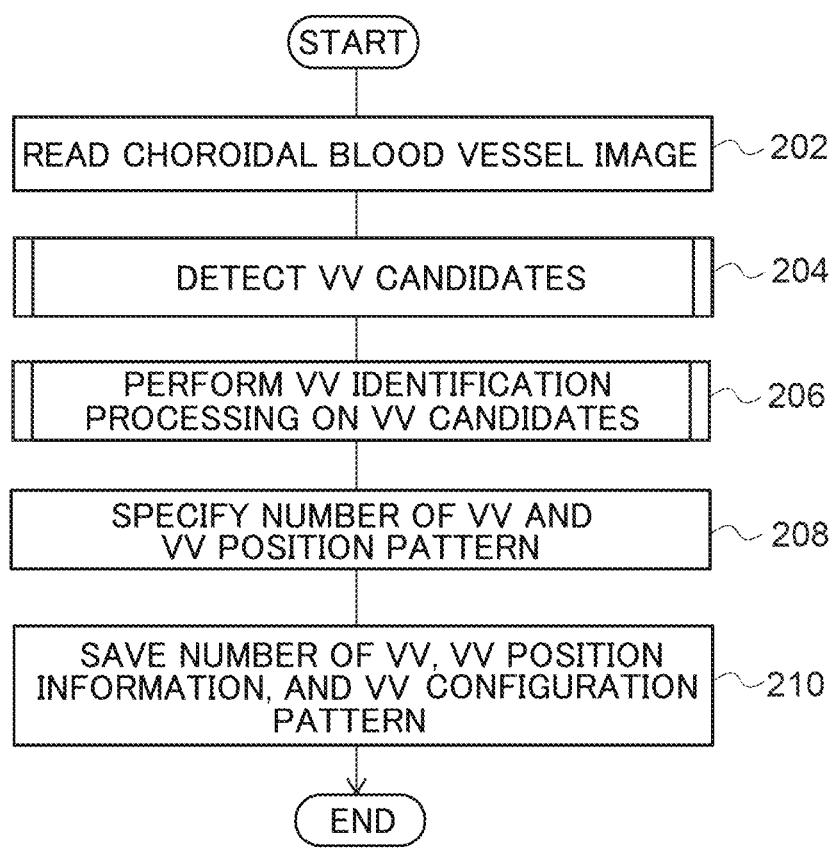
FIG. 5 is a flowchart for an image processing program.

Next, the image processing performed by the management server 140 will be described in detail using FIG. 5. As a result of the CPU 162 of the management server 140 executing the image processing program, the image processing shown in the flowchart in FIG. 5 is performed.

The image processing program is executed when the management server 140 generates a choroidal blood vessel image based on image data for a fundus image photographed by the ophthalmic device 110.

The choroidal blood vessel image is generated in the following manner.

Firstly, the information contained in the first fundus image (i.e., the R fundus image) and the second fundus image (i.e., the G fundus image) will be described.

The structure of an eye is such that a plurality of layers having mutually different structures cover a vitreous humor. Included among the plurality of layers are the retina, the choroid, and the sclera going from the innermost side on the vitreous humor side towards the outer side. R light travels through the retina and reaches the choroid. Accordingly, information about blood vessels present in the retina (i.e., retinal blood vessels) and information about blood vessels present in the choroid (i.e., choroidal blood vessels) are contained in the first fundus image (i.e., the R fundus image). In contrast to this, G light only reaches as far as the retina. Consequently, only information about blood vessels present in the retina (i.e., retinal blood vessels) is contained in the second fundus image (i.e., the G fundus image).

Figure 8:
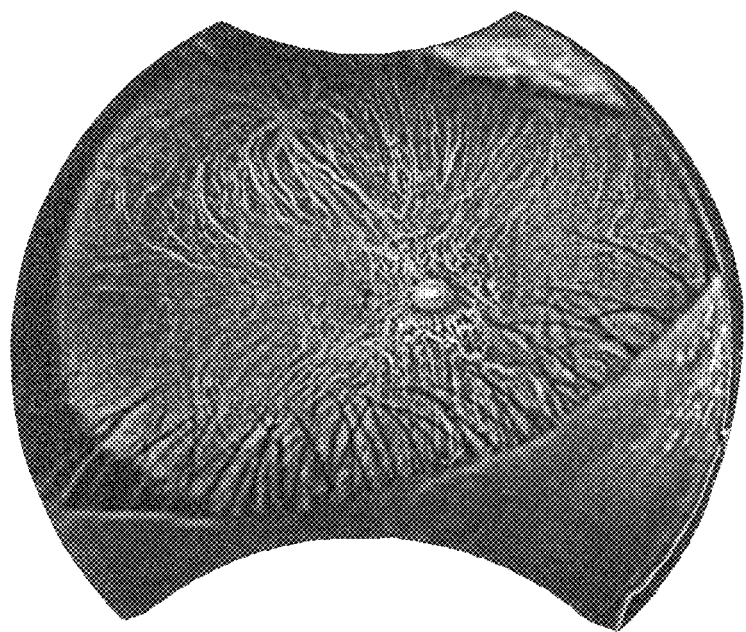
FIG. 8 is a view showing a choroidal blood vessel image.

As a result of the image processing unit 182 of the management server 140 performing black-hat filtering on the second fundus image (i.e., the G fundus image), the retinal blood vessels are extracted from the second fundus image (i.e., the G fundus image). Next, the image processing unit 182 removes the retinal blood vessels from the first fundus image (i.e., the R fundus image) by performing inpainting using the retinal blood vessels extracted from the second fundus image (i.e., the G fundus image). In other words, the image processing unit 182 performs processing to paint the retinal blood vessel structure of the first fundus image (i.e., the R fundus image) so that this retinal blood vessel structure has the same value as the surrounding pixels using position information for the retinal blood vessels extracted from the second fundus image (i.e., the G fundus image). Next, the image processing unit 182 enhances the choroidal blood vessels in the first fundus image (i.e., the R fundus image) by performing CLAHE (Contrast Limited Adaptive Histogram Equalization) processing on the image data for the first fundus image (i.e., the R fundus image) from which the retinal blood vessels have been removed. As a result, the choroidal blood vessel image shown in FIG. 8 is obtained. The choroidal blood vessel image hereby generated is stored in the memory 164.

Moreover, it should be noted that although this choroidal blood vessel image is generated from the first fundus image (i.e., the R fundus image) and the second fundus image (i.e., the G fundus image), it is also possible for the image processing unit 182 to generate the choroidal blood vessel image using the first fundus image (i.e., the R fundus image) and the IR fundus image that was photographed using IR light. The method used to generate a choroidal blood vessel image is described in Japanese Patent Application No. 2018-052246 filed on Mar. 20, 2018 and this disclosure is incorporated by reference in its entirety into the present application.

When the image processing program is started, in step 202 shown in FIG. 5, the image processing unit 182 reads the choroidal blood vessel image (see FIG. 8) from the memory 164.

In step 204, the image processing unit 182 detects vortex vein (hereinafter, referred to as 'VV') candidates in the choroidal blood vessel image. The processing of step 204 is described below in detail. Here, the vortex veins (VV) are outflow paths of a blood flow into the choroid, and between four and six vortex veins are present near the posterior polar side of the equatorial plane of an eyeball.

In step 206, the image processing unit 182 calculates an identification probability for a VV candidate that shows whether or not that VV candidate is a VV, and executes VV identification processing (described below in detail) in order to set an identification flag (i.e., a VV flag/or a non-VV flag). The processing of step 206 is also described below in detail.

Figure 9:
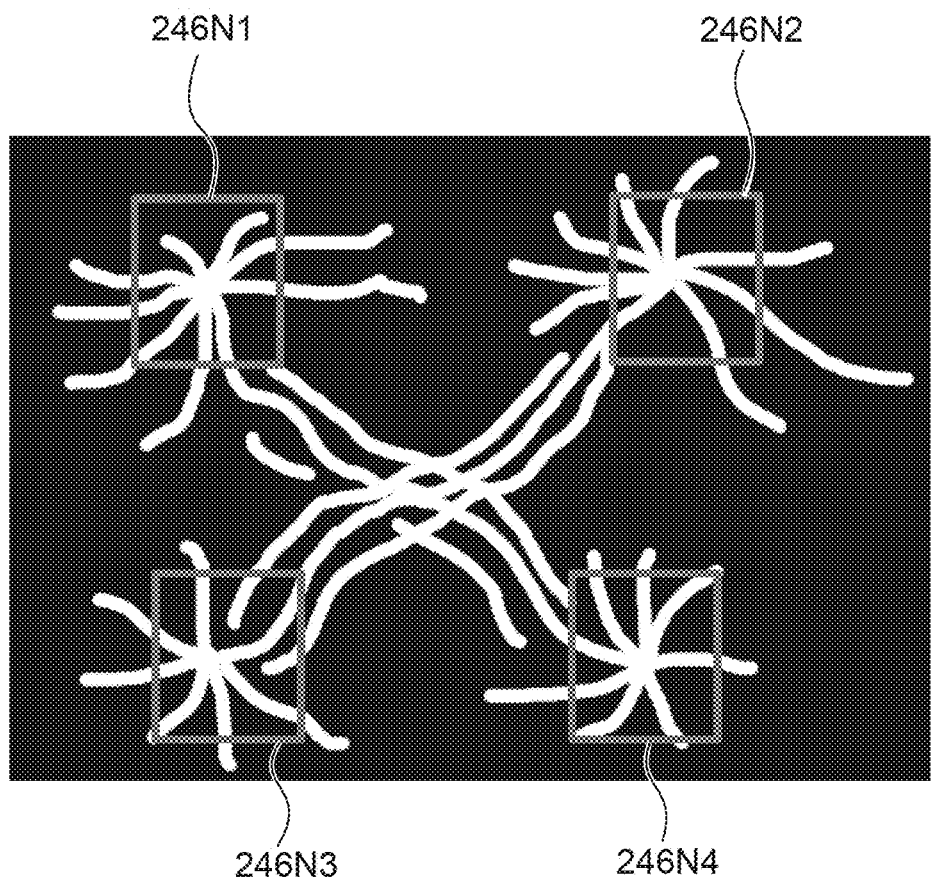
FIG. 9 is a view showing an image in which positions of VV that have been verified as VV are displayed superimposed on a fundus image.

In step 208, the image processing unit 182 specifies the number of VV, and also specifies a VV configuration pattern (i.e., the configuration of a plurality of VV). This VV configuration pattern is information showing what kind of configuration the plurality of VV positions are arranged in on the fundus. If the number of VV is four, then as is shown in FIG. 9, it is common for the VV to be located in the four corners of the choroidal blood vessel image. In FIG. 9, the symbols 246N1, 246N2, 246N3, and 246N4 show frames that are used to specify the VV positions.

In step 210, the processing unit 186 saves data including the number of VV, position information for the VV (i.e., coordinates showing the VV positions on the choroidal blood vessel image; these coordinates are saved for each of the VV), the VV configuration pattern, the identification flags (i.e., a VV flag/or a non-VV flag), and the identification probability in the memory 164. These data items are used to create a display screen for a choroidal blood vessel analysis mode (described below).

Figure 6:
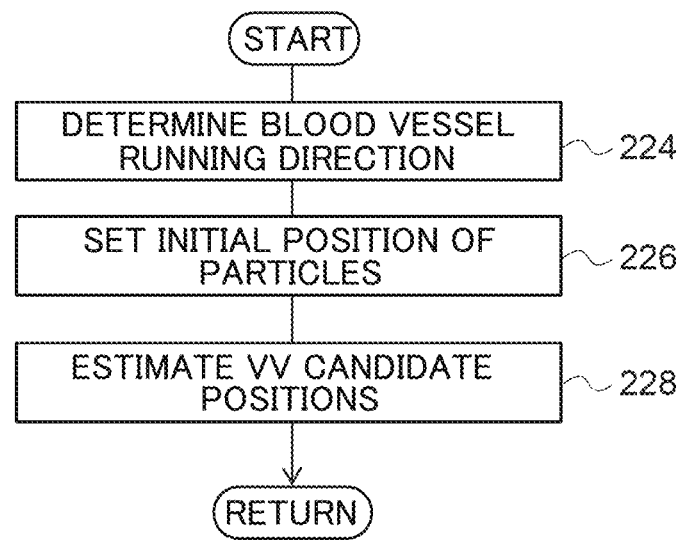
FIG. 6 is a flowchart for a first VV candidate detection processing program.

Next, the processing of step 204 will be described in detail. In the processing of step 204, the VV detected in the first VV candidate detection processing shown in FIG. 6 are set as VV candidates. A flowchart for a first VV candidate detection processing program is shown in FIG. 6.

In step 224, the image processing unit 182 determines the blood vessel running direction of each pixel in the choroidal blood vessel image. More specifically, the image processing unit 182 repeatedly performs the processing described below on all of the pixels. Namely, the image processing unit 182 sets an area (i.e., a cell) that is formed by a plurality of pixels surrounding a central pixel. Next, a gradient direction (shown by an angle not less than 0 degrees and less than 180 degrees (note that 0 degrees is defined as the direction of a straight line (i.e., a horizontal line))) of the brightness of each pixel in the cell is calculated based on the brightness value of the pixels surrounding the pixel that is the subject of the calculation. This calculation of the gradient direction is performed for all of the pixels in the cell.

Next, in order to create a histogram having 9 bins whose gradient directions are 0 degrees, 20 degrees, 40 degrees, 60 degrees, 80 degrees, 100 degrees, 120 degrees, 140 degrees, and 160 degrees (i.e., the width of each bin is 20 degrees), the number of pixels within each cell of the gradient direction corresponding to each bin is counted. The width of one bin of the histogram corresponds to 20 degrees, and the number of pixels (i.e., the count value) within the cell having a gradient direction of not less than 0 degrees and less than 10 degrees and not less than 170 degrees and less than 180 degrees is set in the bin for 0 degrees. In the bin for 20 degrees is set the number of pixels (i.e., the count value) within the cell having a gradient direction of not less than 10 degrees and less than 30 degrees. In the same way, the count values are also set for the bins of the angles of 40 degrees, 60 degrees, 80 degrees, 100 degrees, 120 degrees, 140 degrees, and 160 degrees. Because there are nine bins in the histogram, the blood vessel running directions of the pixels can be defined as any one of nine types of directions. Note that, by narrowing the width of the bins and thereby increasing the number of bins, it is possible to raise the resolution of the blood vessel running direction. Standardization is performed on the count value of each bin (i.e., along the vertical axis of the histogram), and a histogram is created for the analysis points.

Next, the image processing unit 182 specifies the blood vessel running directions of the analysis points from the histogram. More specifically, the image processing unit 182 specifies the bin of the angle having the smallest count value (as an example, 60 degrees), and specifies 60 degrees, which is the gradient direction of the specified bin as the blood vessel running direction of the pixels. Note that the reason why the gradient direction having the smallest count value is taken as the blood vessel running direction is as follows. Namely, the brightness gradient is smallest in the blood vessel running direction, and the brightness gradient is larger in all other directions (for example, the difference in brightness is large between blood vessels and all other portions). Accordingly, if a histogram of the brightness gradient of each pixel is created, then the count value of the bin relative to the blood vessel running direction decreases. In the same way, a histogram is created for each pixel in the choroidal blood vessel image, and the blood vessel running direction of each pixel is calculated. The calculated blood vessel running direction of each pixel is stored in the memory 164.

Note that the blood vessel running direction is an example of the 'choroidal blood vessel structure' of the technology of the present disclosure.

In step 226, the image processing unit 182 sets initial positions for a total of L number of virtual particles (namely, M number of virtual particles in a vertical direction and N number of virtual particles in a horizontal direction) at equidistant intervals on the choroidal blood vessel image. For example, a total number L of 500 (when M=10, and N=50) initial positions are set.

In step 228, the image processing unit 182 acquires the blood vessel running direction of an initial position (i.e., one of the L number thereof), and the virtual particles are moved a predetermined distance in the acquired blood vessel running direction. The blood vessel running direction at the new position is then acquired once again, and the virtual particles are again moved a predetermined distance in the acquired blood vessel running direction. This moving of the virtual particles a predetermined distance in the blood vessel running direction is repeated for a preset number of movements.

The above-described processing is executed in all of the L number of positions. At the point when the set number of movements have been performed for all of the L number of virtual particles, those points where a fixed number or higher of the virtual particles are concentrated are taken as VV candidates. The VV candidate positions are stored in the memory 164 as first VV candidates.

Figure 7:
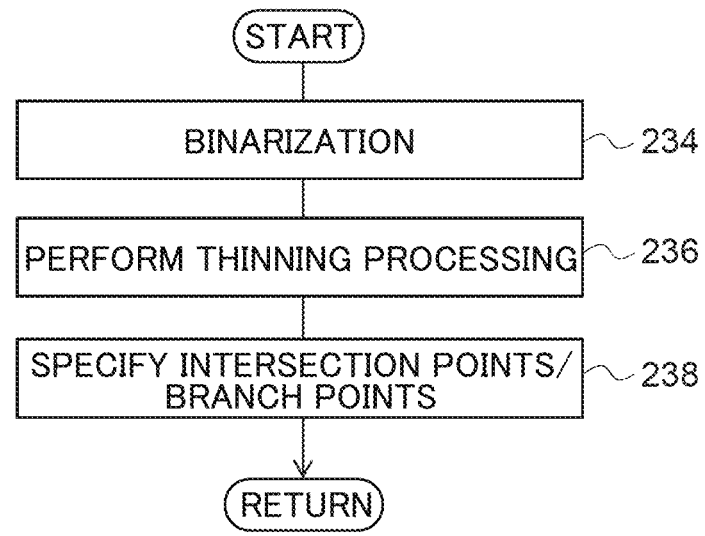
FIG. 7 is a flowchart for a second VV candidate detection processing program.

Instead of the first VV candidate detection processing described in FIG. 6, it is also possible for second VV candidate detection processing (described in FIG. 7) to be employed. A flowchart of a second VV candidate detection processing program is shown in FIG. 7.

Figure 10:
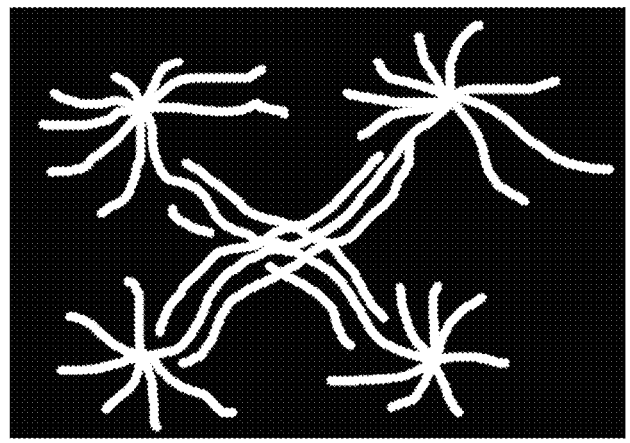
FIG. 10 is a view showing a binarized image of a choroidal blood vessel image.
Figure 11:
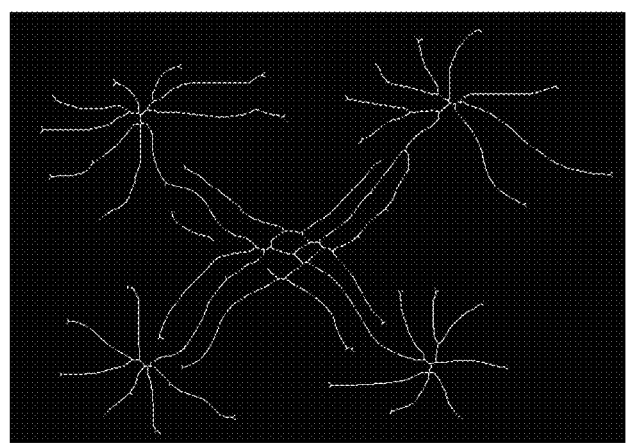
FIG. 11 is a view showing a line image of a binarized image.

In step 234, the image processing unit 182 binarizes the choroidal blood vessel image at a predetermined threshold value so as to generate the binarized image shown in FIG. 10. In step 236, the image processing unit 182 performs thinning processing on the binarized image so as to convert this binarized image into a line image having a width of one pixel (see FIG. 11), and the thickness information is deleted.

Figure 12:
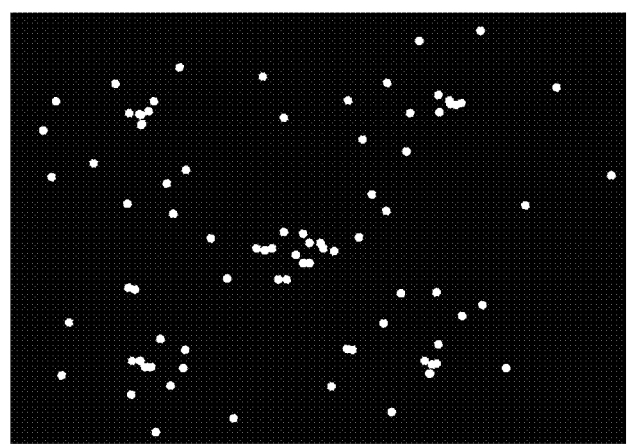
FIG. 12 is a view showing branch points of choroidal blood vessels.

In step 238, as is shown in FIG. 12, in the line image, the image processing unit 182 specifies blood vessel intersection points where lines intersect, blood vessel branch points where lines branch, and blood vessel characteristic points where there is a characteristic pattern. FIG. 12 is a white spot distribution diagram in which the blood vessel intersection points, blood vessel branch points, and blood vessel characteristic points are shown as white spots. These white spots are VV candidate positions.

Note that the blood vessel intersection points, blood vessel branch points, and blood vessel characteristic points are examples of the 'choroidal blood vessel structure' of the technology of the present disclosure.

Next, the VV identification processing of step 206 shown in FIG. 5 will be described with reference to FIG. 13. The VV identification processing is processing to ascertain whether a VV candidate detected in step 204 shown in FIG. 5 is a true VV. In step 252 shown in FIG. 13, the image processing unit 182 sets an identification number n that identifies each one of the plurality of VV candidates to 1. In step 254, the image processing unit 182 selects the VV candidate identified by the identification number n.

In step 256, the image processing unit 182 uses Log-Polar conversion to calculate characteristic quantities in the choroidal blood vessel image peripheral to the VV candidate position for the VV candidate identified by the identification number n. More specifically, firstly, image data for a predetermined area that contains the position of the VV candidate n is extracted from the choroidal blood vessel image. An image of a predetermined area that is centered on the pixel that corresponds to this VV candidate position is then extracted, and Log-Polar conversion is performed on the extracted image.

Figure 14A:
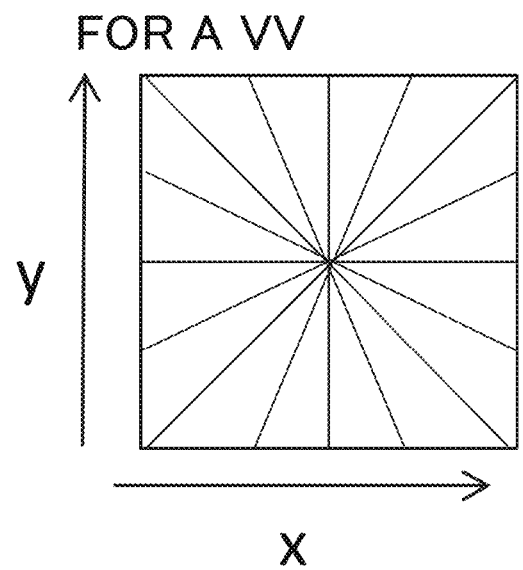
FIG. 14A is a view showing a state when a VV candidate is a true VV.
Figure 14B:
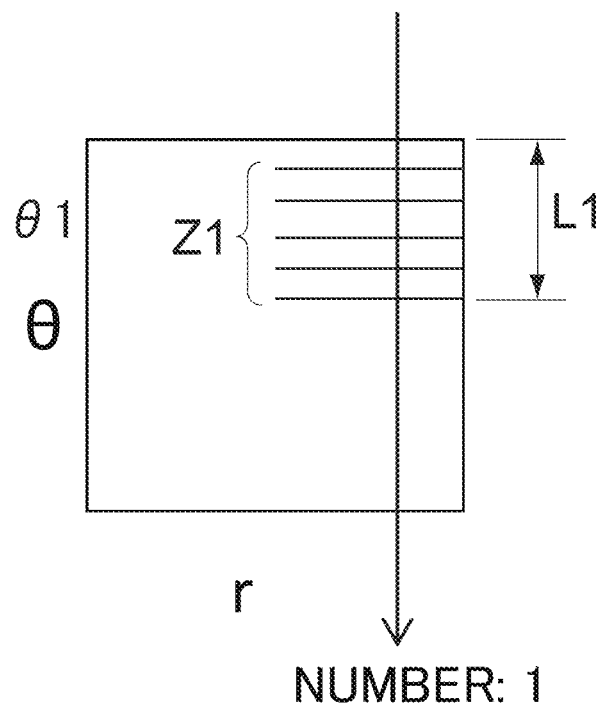
FIG. 14B is a view showing results of Log-Polar processing performed on a true VV.

If the VV candidate n is a true VV, then in the image for the predetermined area that contains the VV candidate position, orientations of the choroidal blood vessels are in a radial configuration centered on the VV candidate position. In other words, as is shown in FIG. 14A, the blood vessels converge at a predetermined position (i.e., the VV candidate position). If Log-Polar conversion is performed on an image in which the blood vessels run in a radial configuration in this way, then as is shown in FIG. 14B, a single stripe pattern Z is created (the pixel values in the area of the stripe pattern are brighter values than in other areas). The width of the area in which this stripe pattern appears (i.e., the width of the stripe pattern in a θ direction) is taken as L1, and a position on a θ axis of a center of the stripe pattern is taken as θ1. A characteristic of this stripe pattern is defined as the unimodality shown in FIG. 16A.

Figure 15A:
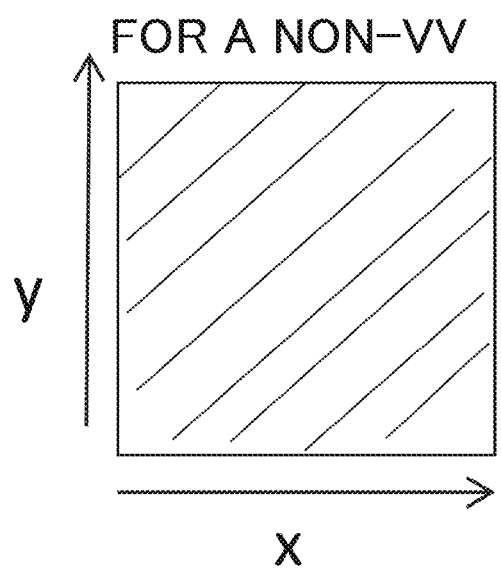
FIG. 15A is a view showing a state when a VV candidate is not a true VV.
Figure 15B:
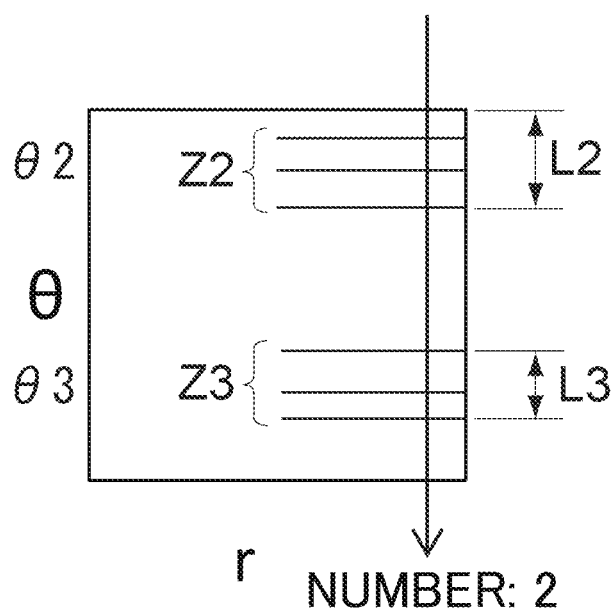
FIG. 15B is a view showing results of Log-Polar processing performed when the VV candidate is not a true VV.

In contrast to this, if the VV candidate is not a true VV, then as is shown in FIG. 15A, the image for the predetermined area that contains the VV candidate position appears as an image containing a plurality of diagonal lines, and the blood vessels do not converge. If Log-Polar conversion is performed on an image containing these diagonal lines, then as is shown in FIG. 15B, two stripe patterns, namely, a stripe pattern Z2 and a stripe pattern Z3 are created. The width of the area in which the stripe pattern Z2 appears (i.e., the width in the θ direction) is taken as L2, and in the same way, the width of the area in which the stripe pattern Z3 appears is taken as L3 (L2<L1, L3<L1). Positions on the θ axis of the center positions of the stripe patterns are taken respectively as θ2 and θ3. A characteristic of these stripe patterns is defined as the multimodality show in FIG. 16C. Note that the characteristic of these stripe patterns may also be defined as the bimodality show in FIG. 16B.

Figure 16A:
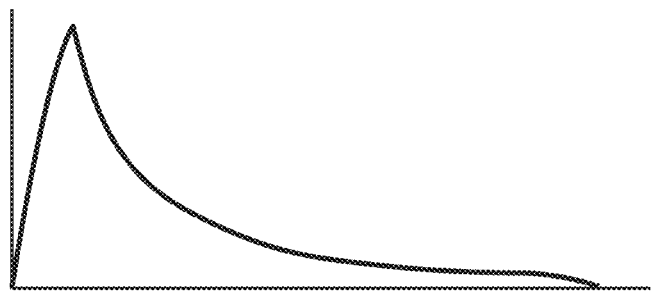
FIG. 16A is a first graph created when processing is performed to integrate pixel values in an R direction at each θ direction shown in FIG. 14A or FIG. 15A, when the horizontal axis is taken as θ, and the vertical axis is taken as the integrated pixel value.
Figure 16B:
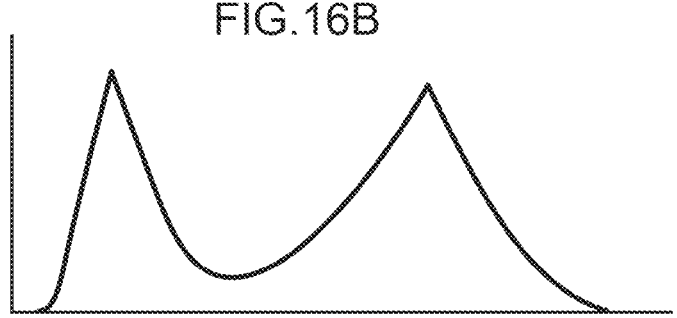
FIG. 16B is a second graph created when processing is performed to integrate pixel values in an R direction at each θ direction shown in FIG. 14A or FIG. 15A, when the horizontal axis is taken as θ, and the vertical axis is taken as the integrated pixel value.
Figure 16C:
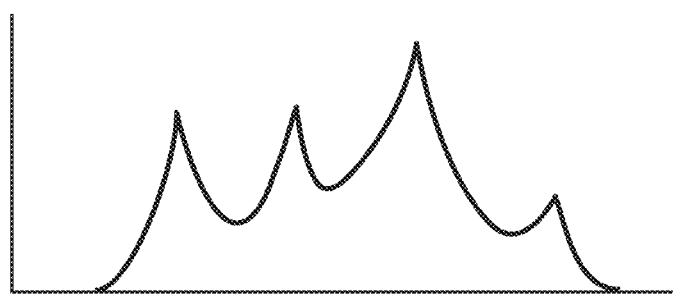
FIG. 16C is a third graph created when processing is performed to integrate pixel values in an R direction at each θ direction shown in FIG. 14A or FIG. 15A, when the horizontal axis is taken as θ, and the vertical axis is taken as the integrated pixel value.

In this step 256, the images that have undergone Log-Polar conversion are analyzed, and characteristic quantities that show whether the configuration is unimodal or multimodal are calculated. Processing to integrate the pixel values in the R direction in each of the θ directions shown in FIG. 14A or FIG. 15A is then performed, and as is shown in FIG. 16A through FIG. 16C, graphs are created whose horizontal axis shows θ and whose vertical axis shows the integrated pixel values. Physical quantities showing the shape of these graphs are taken as the characteristic quantities. A graph such as that in FIG. 16A having a single mountain is called unimodal, a graph such as that in FIG. 16B having two mountains is called bimodal, and a graph such as that in FIG. 16C having three or more mountains is called multimodal. For example, physical quantities such as the number of mountains, the position of the peak of each mountain on the θ axis, and the width of each mountain are taken as characteristic quantities.

In step 258, the image processing unit 182 calculates the identification probability of a VV candidate based on these characteristic quantities. The identification probability of a VV candidate is determined by the aforementioned characteristic quantities. For example, if the number of mountains is taken as n, the position of the peak of each mountain on the θ axis is taken as θ, and the width of each mountain is taken as W, then an identification probability P of a VV candidate is expressed as a function f(n, θ, W) of n, θ, and W. Namely, $$P = f(n, \theta, W)$$

As has been described above, because an image in which the orientations of the choroidal blood vessels are in a radial configuration from a center position, such as that shown in FIG. 14A, shows unimodality after the Log-Polar conversion, the identification probability increases when the characteristic quantities show unimodality. On the other hand, because an image formed by diagonal lines, such as that shown in FIG. 15A, shows multimodality after the Log-Polar conversion, the identification probability decreases. Furthermore, even though both images may show unimodality, a mountain having a sharp peak (i.e., a mountain having a narrow width) has greater probability of identification than a mountain with a gentle peak (i.e., a mountain having a broad width). Accordingly, by analyzing the characteristic quantities in the form of the graph configurations in FIG. 16A through FIG. 16C, it is possible to determine the identification probability.

In step 260, the image processing unit 182 decides whether or not the determined identification probability is greater than a reference probability (this is a probability that shows a threshold value—for example, a probability of 50%).

If the image processing unit 182 decides that the identification probability is greater than the reference probability, then in step 262, the image processing unit 182 identifies the VV candidate that is identified by the identification number n as being a VV, and attaches VV flag information showing that this VV candidate is a VV to the identification number n. If, however, the image processing unit 182 decides that the identification probability is less than the reference probability, then in step 264, the image processing unit 182 identifies the VV candidate that is identified by the identification number n as not being a VV, and attaches non-VV flag information showing that this VV candidate is not a VV to the identification number n.

In step 266, the image processing unit 182 determines whether or not the above-described processing (i.e., step 254 through step 266) has been completed for all of the VV candidates by determining whether or not the identification number n is the same number as a total number N of VV candidates. If it is not determined that the above-described processing (i.e., step 254 through step 266) has been completed for all of the VV candidates, then in step 268, the image processing unit 182 increments the identification number n by 1. Thereafter, the VV identification processing returns to step 254. If, however, it is determined that the above-described processing (i.e., step 254 through step 266) has been completed for all of the VV candidates, then in step 268, then the VV identification processing is ended.

(Image Viewer 150 Choroidal Blood Vessel Analysis Mode)

Next, the data on the display screen for the choroidal blood vessel analysis mode will be described. The management server 140 holds content data (i.e., image data as well as various other types of data (described below)) that it displays on the choroidal blood vessel analysis mode screen.

Firstly, as is described above, image data for a fundus image (i.e., a first fundus image (i.e., a red fundus image) and a second fundus image (i.e., a G fundus image)) is transmitted from the ophthalmic device 110 to the management server 140, so that this image data for a fundus image (i.e., a first fundus image (i.e., a red fundus image) and a second fundus image (i.e., a G fundus image)) is held in the management server 140. The management server 140 holds image data for a choroidal blood vessel image (see FIG. 8), image data for an image in which the positions of VV that have been verified as being VV are displayed superimposed on a fundus image (see FIG. 10), and data for the VV positions, the number of VV, and the VV configuration pattern.

When the fundus of a patient is being photographed, individual information pertaining to that patient is input into the ophthalmic device 110. This individual information includes the patient's ID, name, age, eyesight and the like. When the fundus of the patient is photographed, information showing whether the eye whose fundus is photographed is the right eye or the left eye is also input. In addition, when the fundus of a patient is photographed, the date and time of the photograph are also input. The data for the individual information, the right eye/left eye information, and the date and time of the photograph are transmitted from the ophthalmic device 110 to the management server 140. The management server 140 holds this data for the individual information, the right eye/left eye information, and the date and time of the photograph.

In addition, the eye axial length of the patient is measured by the eye axial length measurement device 120, and data for the eye axial length of the patient is transmitted from the eye axial length measurement device 120 to the management server 140 so as to correspond to that patient's ID. The management server 140 then holds this eye axial length data.

Accordingly, as is described above, the management server 140 holds the above-described content data that it displays on the choroidal blood vessel analysis mode screen.

When an ophthalmologist is diagnosing a patient, they perform the diagnosis while viewing the display screen for the choroidal blood vessel analysis mode that is displayed on the image viewer 150. In this case, the ophthalmologist transmits a request to display the choroidal blood vessel analysis mode screen to the management server 140 via the image viewer 150 using a menu screen (not shown in the drawings). When the management server 140 receives this request, the display control unit 184 thereof creates a display screen for the choroidal blood vessel analysis mode on the image viewer 150 using the contents data for the specified patient ID, and the processing unit 186 thereof transmits the image data for the display screen.

Note that the processing unit 186 is an example of an 'output unit' of the technology of the present disclosure.

Figure 17:
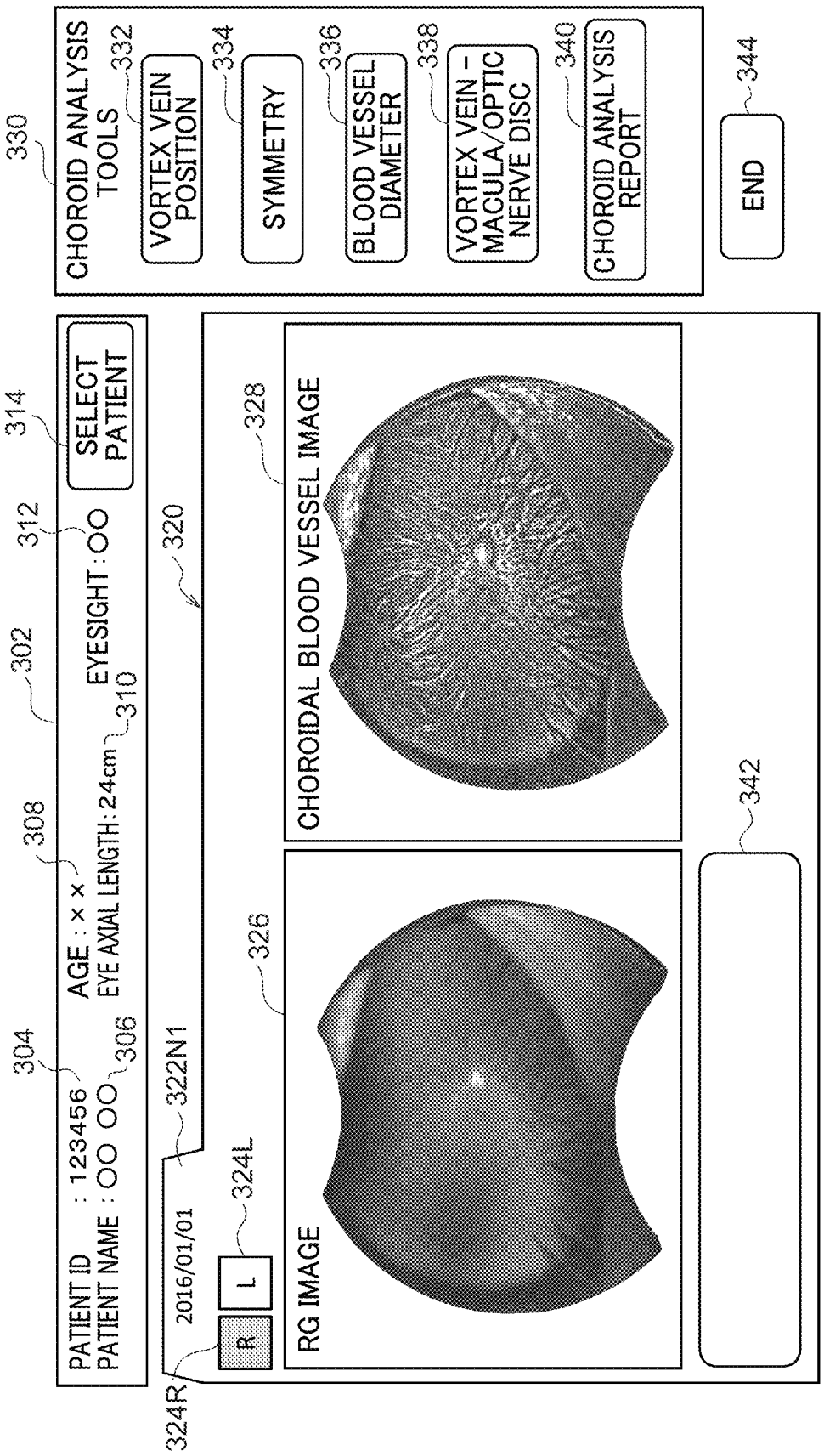
FIG. 17 is a view showing a display screen 300 for a choroidal blood vessel analysis mode.

When the image viewer 150 receives this image data for a display screen for choroidal blood vessel analysis mode, it displays a display screen 300 for choroidal blood vessel analysis mode shown in FIG. 17 on the display of the image viewer 150.

Here, the display screen 300 for choroidal blood vessel analysis mode shown in FIG. 17 will be described. As is shown in FIG. 17, the display screen 300 for choroidal blood vessel analysis mode has an individual information display column 302 that displays individual information pertaining to the patient, an image display column 320, and a choroid analysis tool display column 330.

The individual information display column 302 has a patient ID display column 304, a patient name display column 306, an age display column 308, an eye axial length display column 310, an eyesight display column 312, and a select patient icon 314. Various types of information are displayed in the patient ID display column 304, patient name display column 306, age display column 308, eye axial length display column 310, and eyesight display column 312. Note that when the select patient icon 314 is clicked on, a list of patients is displayed on the display 172 of the image viewer 150, and a user (i.e., an ophthalmologist or the like) is able to select the patient to be analyzed.

The image display column 320 has a photograph date display column 322N1, a right eye information display column 324R, a left eye information display column 324L, and RG image display column 326, a choroidal blood vessel image display column 328, and an information display column 342. Note that the RG image is an image which is obtained by synthesizing the first fundus image (i.e., the R fundus image) and the second fundus image (i.e., the G fundus image) with the size of each pixel value set at a predetermined ratio (for example, 1:1).

The choroid analysis tool display column 330 is provided with a plurality of choroid analysis tools that command the image viewer 150 to perform various types of processing such as, for example, a vortex vein position icon 332, a symmetry icon 334, a blood vessel diameter icon 336, a vortex vein—macula/optic nerve disc icon 338, and a choroid analysis report icon 340. The vortex vein position icon 332 commands that the vortex vein position be specified. The symmetry icon 334 commands that the symmetry of the vortex vein be analyzed. The blood vessel diameter icon 336 commands that a tool that analyzes the diameter of the choroidal blood vessel be employed. The vortex vein—macula/optic nerve disc icon 338 commands that the relative positions between the vortex vein, the macula, and the optic nerve disc be analyzed. The choroid analysis report icon 340 commands that a choroid analysis report be displayed.

Icons and buttons that are used to command that an image (described below) be generated are displayed on the display screen (described below) of the image viewer 150. When a user (such as an ophthalmologist or the like) of the image viewer 150 clicks on an icon or the like, a command signal corresponding to the clicked icon or the like is transmitted from the image viewer 150 to the management server 140. The management server 140 that receives the command signal from the image viewer 150 then generates an image that corresponds to the command signal, and transmits image data for the generated image to the image viewer 150. The image viewer 150 that receives the image data from the management server 140 displays the image on the display 172 based on the received image data. The processing performed by the management server 140 to generate a display screen is implemented by means of a display screen generation program operated by the CPU 162.

In the example shown in FIG. 17, an RG image and a choroid blood vessel image generated when the fundus of the right eye of a patient (the icon 324R has been highlighted) identified by the patient ID number 123456 was photographed on Jan. 1, 2016 are displayed.

Figure 18:
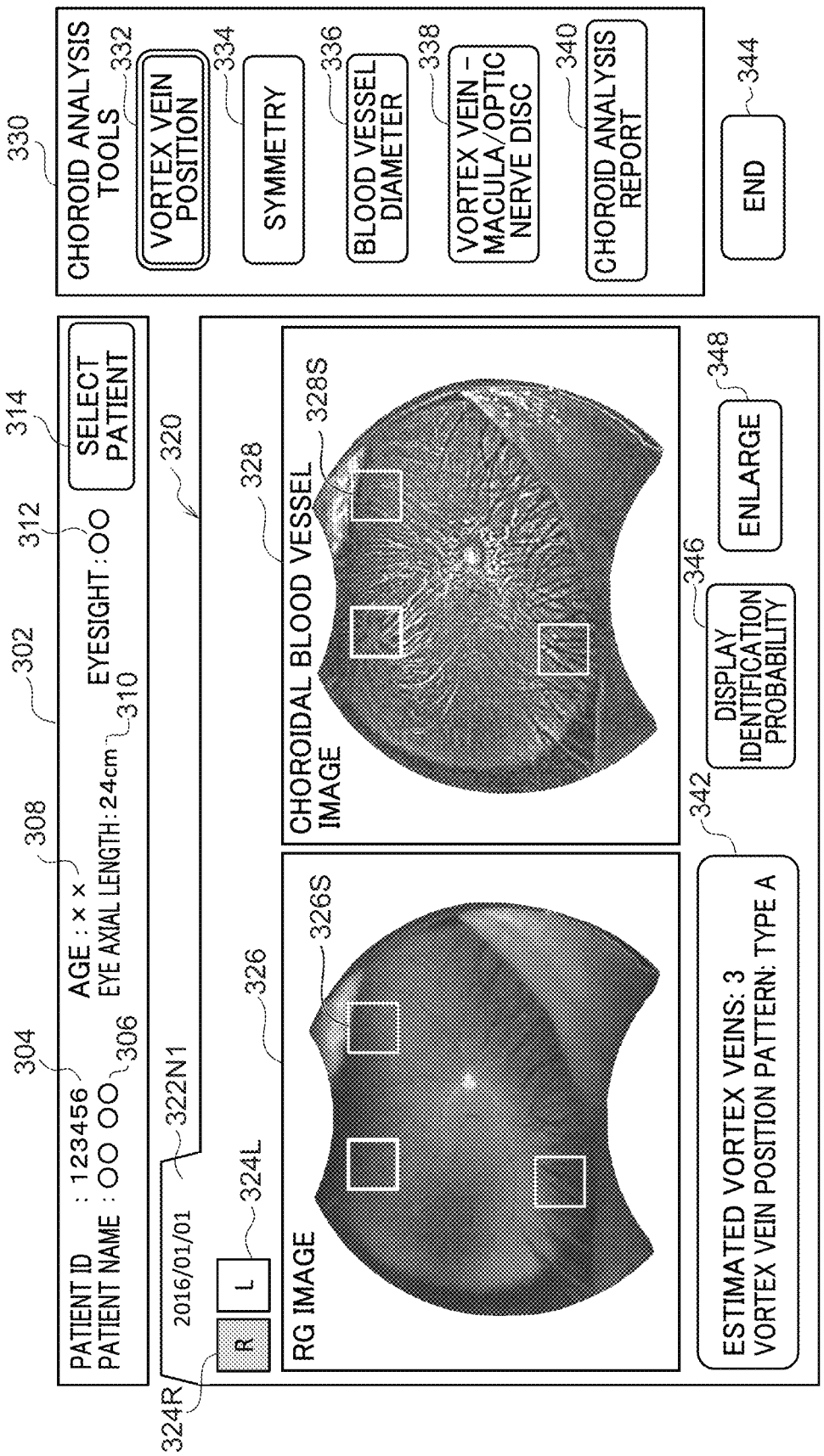
FIG. 18 is a display screen that is displayed when a vortex vein position icon 332 has been clicked on on the display screen shown in FIG. 17.

When the vortex vein position icon 332 in the choroid analysis tool display column 330 shown in FIG. 17 is clicked on, the display screen is altered to a display screen displaying information relating to vortex veins shown in FIG. 18. As is shown in FIG. 18, based on the positions of the VV, the image viewer 150 displays rectangles (326S, 328S) that are centered on the positions of the VV in the RG image in the RG image display column 326 and in the choroidal blood vessel image in the choroidal blood vessel image display column 328. Note that in FIG. 17, it is also possible for only the RG image or the choroidal blood vessel image to be displayed, and for rectangles to be displayed on this displayed image based on the positions of the VV.

The choroidal blood vessel image in which the rectangles 326S and 328S are displayed in the choroidal blood vessel image display column 328 is an example of a 'vortex vein position-superimposed fundus image' of the technology of the present disclosure, and the rectangles 326S and 328S are example of the 'marks' of the technology of the present disclosure.

In addition, based on the number of VV and the VV position pattern, the image viewer 150 displays the number of VV as being 3, and the VV configuration pattern as being Type A in the information display column 342. An identification probability display icon 346 and an enlarge icon 348 are displayed in the image display column 320. The VV configuration pattern is not only the number and positions of vortex veins (VV) actually detected, but it is also possible to consider portions that are hidden by an eyelid and have not been photographed, and to estimate the number and positions of VV in these portions.

Figure 19:
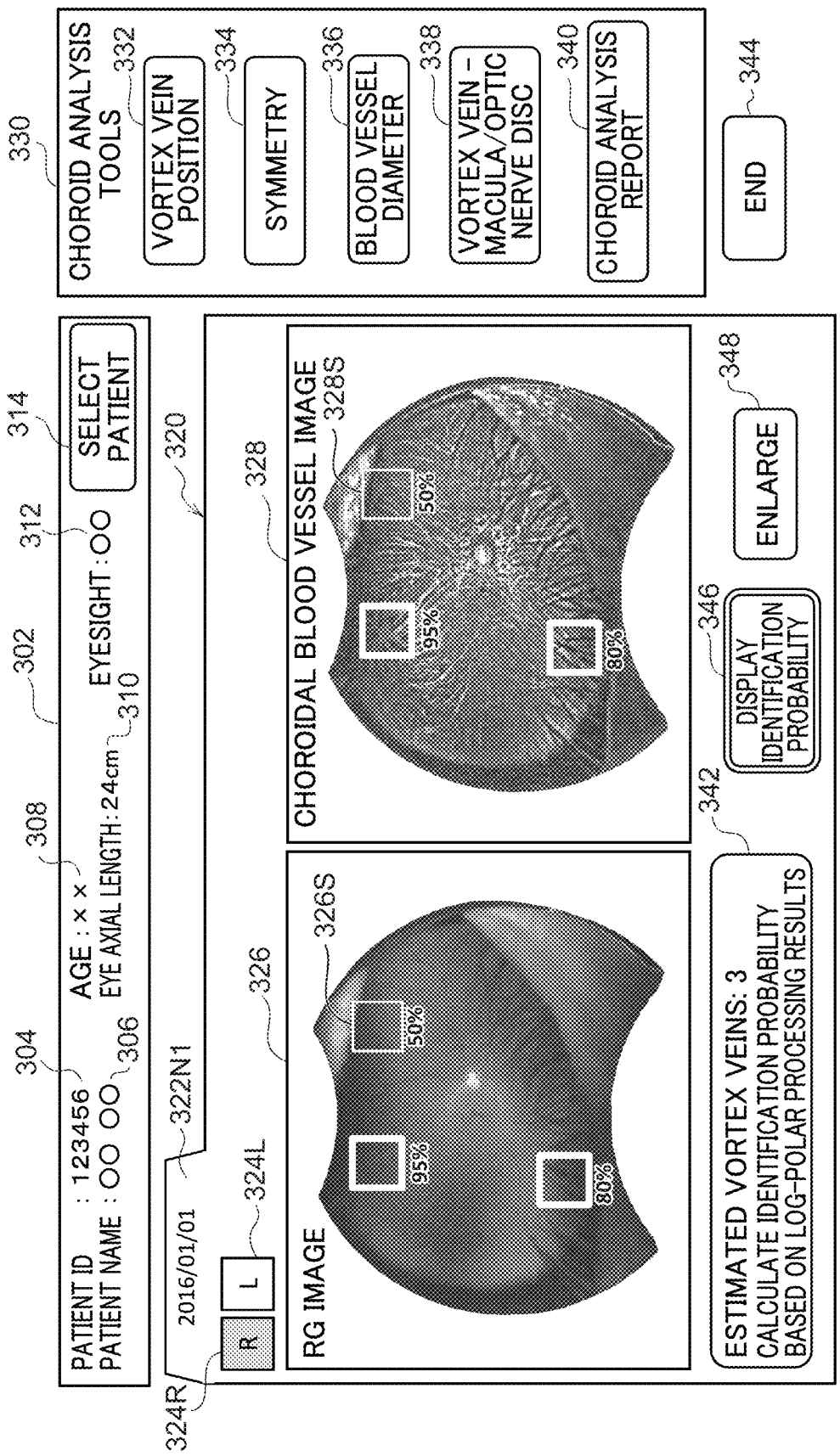
FIG. 19 is a display screen that is displayed when an identification probability display icon 346 has been clicked on on the display screen shown in FIG. 18.

When the identification probability display icon 346 is clicked on, the display screen is altered to a display screen shown in FIG. 19 in which the identification probability is reflected for each VV. As is shown in FIG. 19, the image viewer 150 displays identification probabilities (for example, 95%, 80%, 50%) that show the probability that a VV candidate is a VV in the rectangles 326S and 328S. The image viewer 150 additionally displays in the information display column 342 the number of VV as being three, as well as text stating 'Calculate identification probability based on Log-Polar processing results'.

Figure 20:
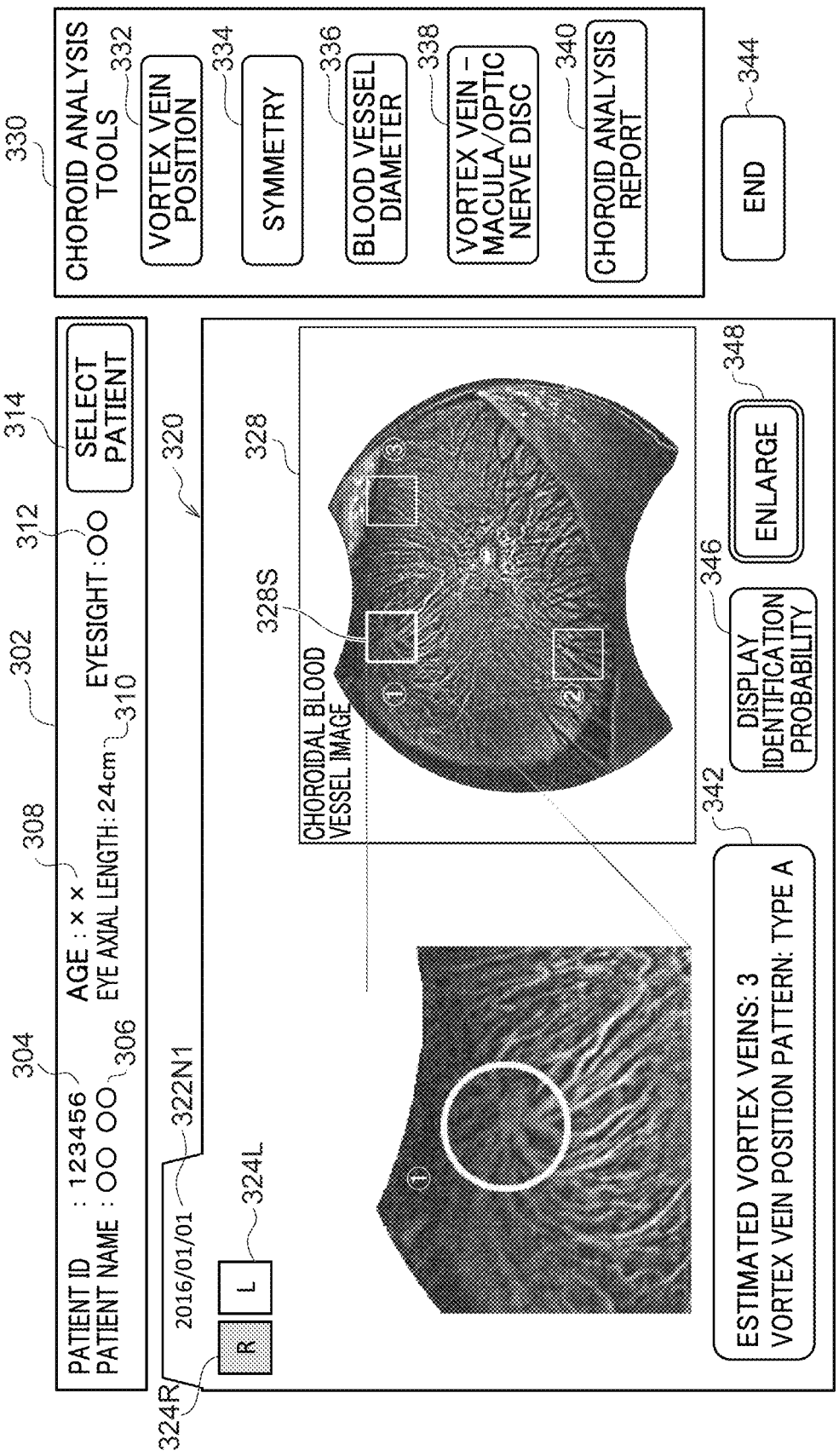
FIG. 20 is a display screen that is displayed when an enlarge icon 348 has been clicked on on the display screen shown in FIG. 18.

If, in the display screen shown in FIG. 18, the enlarge icon 348 is clicked on, a display screen showing an enlargement of an area that contains a VV is displayed. As is shown in FIG. 20, if the rectangle 328S is clicked on, the image viewer 150 displays an enlarged image of the clicked VV portion instead of the RG image display column 326.

As has been described above, in the present exemplary embodiment, positions of vortex veins (VV) are detected from a choroidal blood vessel image, and marks showing these vortex vein positions are displayed superimposed on the choroidal blood vessel image.

In addition, by using an SLO unit that utilizes a wide-angle optical system, it is possible to obtain an ultrawide angle UWF-SLO image having a range of 200 degrees or more as an angle from the center of the eyeball. By using a UWF-SLO image, it is possible to detect vortex veins present in the vicinity of the equatorial plane of the eyeball.

Next, several variant examples of the of the technology of the present disclosure will be described.

First Variant Example

In the first VV candidate detection processing shown in FIG. 6 and the second VV candidate detection processing shown in FIG. 7 of the above-described embodiment, in order to reduce the calculation load, instead of using the entire choroidal blood vessel image, it is possible for an area in which there is a statistically high probability of vortex veins (VV) being present to be set as the detection subject area.

Second Variant Example

It is also possible for the calculation of the characteristic quantities (i.e., step 256 shown in FIG. 13) in the above-described exemplary embodiment to be decided by AI (Artificial Intelligence). It is also possible for a non-explicit stripe pattern in the form of a hidden layer structure or the like to be specified using a method such as deep learning or the like.

Third Variant Example

In the above-described exemplary embodiment, the management server 140 executes the image processing program previously shown in FIG. 5, however, the technology of the present disclosure is not limited to this. For example, the following method may also be employed. When the vortex vein position icon 332 shown in FIG. 17 is clicked on, the image viewer 150 transmits a vortex vein position detection command to the management server 140. In accordance with this, the management server 140 executes step 202 and 204 of the image processing program shown in FIG. 5, and the display screen shown in FIG. 18 is displayed. Furthermore, when the identification probability display icon 346 is clicked on, the image viewer 150 transmits a command to calculate the identification probability to the management server 140. In accordance with this, the management server 140 executes step 206 and 208 shown in FIG. 5, and the display screen shown in FIG. 19 is displayed.

Fourth Variant Example

In the above-described exemplary embodiment, an example in which a fundus image having an internal light irradiation angle of approximately 200 degrees is acquired by the ophthalmic device 110 is described. However, the technology of the present exemplary embodiment is not limited to this, and it is also possible for the fundus image to be photographed using an ophthalmic device having an internal irradiation angle of 100 degrees or less. Moreover, the technology of the present disclosure may also be applied to a montage image that is created by synthesizing together a plurality of fundus images.

Fifth Variant Example

In the above-described exemplary embodiment, fundus images are acquired by the ophthalmic device 110 that is provided with an SLO photographic unit, however, it is also possible for the fundus images to be acquired by a fundus camera that is capable of photographing choroidal blood vessels. Moreover, the technology of the present disclosure may also be applied to images obtained via OCT angiography.

Sixth Variant Example

In the above-described exemplary embodiment, the management server 140 executes the image processing program, however, the technology of the present disclosure is not limited to this. For example, it is also possible for the image processing program to be executed by the ophthalmic device 110 or the image viewer 150.

Seventh Variant Example

In the above-described exemplary embodiment, the ophthalmic system 100 provided with the ophthalmic device 110, the eye axial length measurement device 120, the management server 140, and the image viewer 150 is described as an example, however, the technology of the present disclosure is not limited to this. It is also possible, as a first example, for the eye axial length measurement device 120 to be omitted, and for the ophthalmic device 110 to additionally perform the functions of the eye axial length measurement device 120. Furthermore, it is also possible, as a second example, for the ophthalmic device 110 to additionally perform the functions of at least one of the management server 140 and the image viewer 150. For example, if the ophthalmic device 110 also has the functions of the management server 140, then the management server 140 may be omitted. In this case, the image processing program is executed by the ophthalmic device 110 or the image viewer 150. In the same way, if the ophthalmic device 110 also has the functions of the image viewer 150, then the image viewer 150 may be omitted. As a third example, it is also possible for the management server 140 to be omitted, and for the image viewer 150 to additionally execute the functions of the management server 140.

Other Variant Examples

The data processing described in the foregoing exemplary embodiment is merely one example thereof. Accordingly, it should be understood that various modifications and the like such as deleting unnecessary steps, adding new steps, and rearranging the processing sequence may be made thereto insofar as they do not depart from the spirit or scope of the present disclosure.

Moreover, in the above-described embodiment, a case is illustrated in which data processing is achieved by means of a software structure which utilizes a computer, however, the technology of the present disclosure is not limited to this. For example, instead of a software structure utilizing a computer, it is also possible for the data processing to be executed solely by means of a hardware structure such as FPGA (Field-Programmable Gate Array) or ASIC (Application Specific Integrated Circuit) or the like. It is also possible for a portion of the data processing to be executed by means of a software structure, and for the remaining processing to be executed by means of a hardware structure.

What is claimed is:

1. An image processing method comprising:
analyzing a fundus image to find a direction of a choroidal blood vessel; and
detecting a position of a vortex vein based on the direction of the choroidal blood vessel.

2. The image processing method according to claim 1, characterized in that a vortex vein position-displayed fundus image in which the vortex vein positions are displayed on the fundus image is generated.

3. The image processing method according to claim 1, wherein the analyzing includes analyzing the choroidal blood vessel running direction.

4. The image processing method according to claim 3, wherein the detecting of the vortex vein position includes detecting a vortex vein candidate based on a choroidal vascular structure and identifying whether or not the vortex vein candidate is a vortex vein.

5. The image processing method according to claim 4, wherein the identification of whether or not the vortex vein candidate is the vortex vein includes analyzing whether or not the choroidal blood vessels in the fundus image converge at the vortex vein candidate position.

6. The image processing method according to claim 4, wherein the identification of whether or not the vortex vein candidate is the vortex vein includes calculating characteristic quantities in a choroidal image of a periphery of the vortex vein candidates.

7. The image processing method according to claim 6, wherein the identification of whether or not the vortex vein candidate is the vortex vein includes calculating an identification probability for the vortex vein candidate based on the characteristic quantities.

8. The image processing method according to claim 4, wherein the choroidal blood vessel structure is the choroidal blood vessel running direction, blood vessel branch points, or blood vessel characteristic points.

9. The image processing method according to claim 1, wherein the analyzing includes analyzing whether or not a orientation of the choroidal blood vessels in the fundus image are in a radial configuration.

10. The image processing method according to claim 1, characterized in that the fundus image is a choroidal blood vessel image in which choroidal blood vessels have been enhanced.

11. The image processing method according to claim 10, characterized in that the choroidal blood vessel image is an image that is created based on a first fundus image photographed using red light, and a second fundus image photographed using green light.

12. The image processing method according to claim 10, characterized in that the choroidal blood vessel image is an image that is obtained by performing image processing on a wide-angle fundus image.

13. The image processing method according to claim 1, characterized in that a detected number of vortex veins is specified.

\* \* \* \* \*